(12) United States Patent
Munson et al.

(10) Patent No.: US 8,097,049 B2
(45) Date of Patent: Jan. 17, 2012

(54) BIODIESEL PURIFICATION BY A CONTINUOUS REGENERABLE ADSORBENT PROCESS

(75) Inventors: James R. Munson, Neshanic Station, NJ (US); Brian S. Cooke, Clarksville, IN (US); Bryan L. Bertram, Floyds Knob, IN (US)

(73) Assignee: The Dallas Group of America, Inc., Whitehouse, NJ (US)

( * ) Notice: Subject to any disclaimer, the term of this patent is extended or adjusted under 35 U.S.C. 154(b) by 301 days.

(21) Appl. No.: 12/366,203

(22) Filed: Feb. 5, 2009

(65) Prior Publication Data

US 2009/0199460 A1    Aug. 13, 2009

Related U.S. Application Data

(60) Provisional application No. 61/063,982, filed on Feb. 7, 2008.

(51) Int. Cl.
*C10L 1/19* (2006.01)
*B01J 49/00* (2006.01)
*C07C 45/54* (2006.01)

(52) U.S. Cl. ........... 44/385; 554/176; 554/191; 210/670

(58) Field of Classification Search .................... 44/308, 44/385; 554/176, 191; 210/195, 198, 263, 210/269, 659, 660, 670, 656, 194, 268
See application file for complete search history.

(56) References Cited

U.S. PATENT DOCUMENTS

| | | | |
|---|---|---|---|
| 2,639,289 A | 5/1953 | Vogel | |
| 4,048,205 A | 9/1977 | Neuzil et al. | |
| 4,144,373 A | 3/1979 | Weiss et al. | |
| 4,664,807 A | 5/1987 | Van Dam et al. | |
| 4,770,819 A | 9/1988 | Zinnen | |
| 4,797,233 A | 1/1989 | Zinnen | |
| 4,977,243 A | 12/1990 | Barder et al. | |
| 5,157,132 A | 10/1992 | Tan et al. | |

(Continued)

FOREIGN PATENT DOCUMENTS

EP    2028259 A1    2/2009

(Continued)

*Primary Examiner* — Cephia D Toomer
*Assistant Examiner* — Pamela H Weiss
(74) *Attorney, Agent, or Firm* — Porzio, Bromberg & Newman, P.C.

(57) ABSTRACT

A quick, economical and environmentally friendly, "green", process for the continuous purification of biodiesel (fatty acid alkyl esters (FAAE)) is described using a powdered, granulated or extruded adsorbent. The adsorbent is contained in a column system and is regenerated for reuse multiple times. The process employs an adsorbent such as, but not limited to, carbon, silica, clay, zeolite or a metal silicate contained in a column to remove the impurities from fatty acid alkyl esters (FAAE) or crude biodiesel in a continuous process. The process utilizes the adsorbent column system for the purification of biodiesel, rather than water or filtration, to remove soaps and other impurities entrained in a crude biodiesel. The crude biodiesel is contacted with an adsorbent packed into a column, or multiple columns in series, for a sufficient amount of time to remove impurities such as, but not limited to, soaps, metals, free glycerin, sterol glucosides and many of the other impurities that reduce the stability of biodiesel. The resulting finished biodiesel exiting the column(s) is ready for the methanol recovery process. Once the adsorbent no longer removes the desired amount of impurities, it is regenerated for reuse. The solvent used for the regeneration process is reclaimed and reused by recycling it back to the transesterification reaction.

21 Claims, 6 Drawing Sheets

U.S. PATENT DOCUMENTS

| | | |
|---|---|---|
| 5,348,755 A | 9/1994 | Roy |
| 5,550,264 A | 8/1996 | Elsasser |
| 5,908,946 A | 6/1999 | Stern et al. |
| 6,982,340 B2 * | 1/2006 | Mumura et al. ............... 554/142 |
| 7,097,770 B2 | 8/2006 | Lysenko et al. |
| 7,592,470 B2 | 9/2009 | Lacome et al. |
| 7,635,398 B2 * | 12/2009 | Bertram et al. ................. 44/605 |
| 2004/0003534 A1 | 1/2004 | Murakami et al. |
| 2005/0056592 A1 * | 3/2005 | Braunger et al. ............. 210/660 |
| 2005/0081436 A1 * | 4/2005 | Bertram et al. ................. 44/605 |
| 2005/0188607 A1 | 9/2005 | Lastella |
| 2005/0245405 A1 | 11/2005 | Geier et al. |
| 2006/0260184 A1 | 11/2006 | Landano |
| 2007/0151146 A1 | 7/2007 | Lee et al. |
| 2007/0158270 A1 * | 7/2007 | Geier et al. ................... 210/656 |
| 2007/0175091 A1 | 8/2007 | Danzer et al. |
| 2007/0175092 A1 | 8/2007 | Ames |
| 2007/0261294 A1 | 11/2007 | Aiken |
| 2007/0282118 A1 * | 12/2007 | Gupta et al. ................... 554/169 |
| 2008/0115407 A1 | 5/2008 | Hoffman |
| 2008/0188676 A1 | 8/2008 | Anderson et al. |
| 2009/0049741 A1 | 2/2009 | Moser |
| 2009/0099380 A1 | 4/2009 | Aiken |
| 2010/0313468 A1 * | 12/2010 | Jalalpoor et al. ................ 44/388 |

FOREIGN PATENT DOCUMENTS

| | | |
|---|---|---|
| WO | 2005037969 A2 | 4/2005 |
| WO | 2005063954 A1 | 7/2005 |
| WO | 2007058485 A1 | 5/2007 |
| WO | 2008011731 A2 | 1/2008 |
| WO | 2008092207 A1 | 8/2008 |
| WO | 2008120223 A2 | 10/2008 |
| WO | 2009009271 A2 | 1/2009 |
| WO | 2009061169 A1 | 5/2009 |
| WO | 2009080287 A2 | 7/2009 |

* cited by examiner

BIODIESEL PURIFICATION BY A CONTINUOUS REGENERABLE ADSORBENT PROCESS

CROSS REFERENCE TO RELATED APPLICATION

This application claims the benefit of U.S. Provisional Patent Application No. 61/063,982, filed Feb. 7, 2008, the entirety of which is hereby incorporated by reference into this application.

BACKGROUND OF THE INVENTION

1. Field of the Invention

The present invention relates to purification of fatty acid alkyl esters (FAAE), in particular, biodiesel, and more particularly, to a process for quick, continuous purification of crude biodiesel by treating crude biodiesel with an adsorbent material contained in one or more columns and regenerating the adsorbent material for re-use.

2. Description of Related Art

Economically viable renewable energy has been a policy goal of governments around the world. One source of renewable fuel that has been promoted and developed is biodiesel. The attraction of biodiesel is the similar properties it possesses in relation to petroleum-based diesel fuel. Biodiesel is a desirable energy alternative to wind, solar, and ethanol derived energy in that the energy content to capital requirement is close to a break-even point, depending, of course, upon the price of petroleum derived energy.

Biodiesel is the purified alkyl esters of fatty acids generally referred to as fatty acid alkyl esters (FAAE). Production of these fatty acid alkyl esters (FAAE) is achieved by the transesterification of animal or vegetable fats or oils or the esterification of fatty acids, including free fatty acids (FFA) found in degraded fat or oil. The process involves the reaction of triacylglycerol with an alcohol, typically methanol, in the presence of a catalyst, typically sodium or potassium hydroxide or methoxide, a reaction referred to as transesterification. Alternately, fatty acids, including those found in degraded fat or oil containing high levels of free fatty acids (FFA), typically referred to as yellow grease, brown grease, or trap grease, are reacted with an alcohol, typically methanol, in the presence of an acid, a reaction referred to as esterification. When using degraded fat or oil as a raw material, esterification is performed prior to transesterification in order to provide for a complete conversion of fatty acids into FAAE. Unreacted methanol from both processes is typically removed by flash evaporation so that it can be reused for the esterification and/or transesterification reaction(s).

However, simply performing the esterification and/or transesterification of fatty acids is not enough to produce a usable biodiesel fuel. Fatty acid alkyl esters (FAAE) contain impurities that can crystallize, foul engines, and cause numerous problems for the user. As a result, regulations have been developed to address the needs of the consumer with respect to quality. Strict standards for commercial biodiesel have been developed by most countries, including the U.S. Government in the specifications set forth in ASTM International's ASTM D6751 and the European Union in the specifications set forth by the European Committee for Standardization in EN 14214.

The specifications for ASTM D6751-07a are as follows:
Biodiesel is defined as the mono alkyl esters of long chain fatty acids derived from vegetable oils or animal fats, for use in compression-ignition (diesel) engines. This specification is for pure (100%) biodiesel prior to use or blending with diesel fuel.

| Property | ASTM Method | Limits | Units |
|---|---|---|---|
| Calcium & Magnesium, combined | EN 14538 | 5 max | ppm (ug/g) |
| Flash Point (closed cup) | D 93 | 93 min. | Degrees C. |
| Alcohol Control (One of the following must be met) | | | |
| 1. Methanol Content | EN14110 | 0.2 Max | % volume |
| 2. Flash Point | D93 | 130 Min | Degrees C. |
| Water & Sediment | D 2709 | 0.05 max. | % vol. |
| Kinematic Viscosity, 40 C. | D 445 | 1.9-6.0 | mm2/sec. |
| Sulfated Ash | D 874 | 0.02 max. | % mass |
| Sulfur | | | |
| S 15 Grade | D 5453 | 0.0015 max. (15) | % mass (ppm) |
| S 500 Grade | D 5453 | 0.05 max. (500) | % mass (ppm) |
| Copper Strip Corrosion | D 130 | No. 3 max. | |
| Cetane | D 613 | 47 min. | |
| Cloud Point | D 2500 | Report | Degrees C. |
| Carbon Residue 100% sample | D 4530* | 0.05 max. | % mass |
| Acid Number | D 664 | 0.50 max. | mg KOH/g |
| Free Glycerin | D 6584 | 0.020 max. | % mass |
| Total Glycerin | D 6584 | 0.240 max. | % mass |
| Phosphorus Content | D 4951 | 0.001 max. | % mass |
| Distillation, T90 AET | D 1160 | 360 max. | Degrees C. |
| Sodium/Potassium. combined | EN 14538 | 5 max | ppm |
| Oxidation Stability | EN 14112 | 3 min | hours |

Workmanship = Free of undissolved water, sediment, & suspended matter
BOLD = BQ-9000 Critical Specification Testing Once Production Process Under Control
*The carbon residue shall be run on the 100% sample.
A considerable amount of experience exists in the US with a 20% blend of biodiesel with 80% diesel fuel (B20). Although biodiesel (B100) can be used, blends of over 20% biodiesel with diesel fuel should be evaluated on a case-by-case basis until further experience is available.
Source: SPECIFICATION FOR BIODIESEL (B100) - ASTM D6751-07a (March 2007).

The specifications for EN 14214 are as follows:

| Property | Unit | Limits Minimum | Limits Maximum | Test method |
|---|---|---|---|---|
| Ester content | % (m/m) | 96.5 | — | EN 14103 |
| Density at 15° C. | kg/m$^3$ | 860 | 900 | EN ISO 3675 |
|  |  |  |  | EN ISO 12185 |
| Viscosity at 40° C. | mm$^2$/s | 3.50 | 5.00 | EN ISO 3104 |
| Flash Point | ° C. | 120 | — | prEN ISO 3679 |
| Sulfur content | mg/kg | — | 10.0 | prEN ISO 20846 |
|  |  |  |  | prEN ISO 20884 |
| Carbon residue | % (m/m) | — | 0.30 | EN ISO 10370 |
| (on 10% distillation residue) |  |  |  |  |
| Cetane number |  | 51.0 | — | EN ISO 5165 |
| Sulfated ash content | % (m/m) | — | 0.02 | ISO 3987 |
| Water content | mg/kg | — | 500 | EN ISO 12937 |
| Total contamination | mg/kg | — | 24 | EN 12662 |
| Copper strip corrosion | rating | class 1 |  | EN ISO 2160 |
| (3 h at 50° C.) |  |  |  |  |
| Oxidation stability 110° C. | hours | 6.0 | — | EN 14112 |
| Acid value | mg KOH/g | — | 0.50 | EN 14104 |
| Iodine value | gr iodine/100 gr | — | 120 | EN 14111 |
| Linolenic acid methyl ester | % (m/m) | — | 12.0 | EN 14103 |
| Polyunsaturated (>=4 double bonds) methyl esters | % (m/m) | — | 1 |  |
| Methanol content | % (m/m) | — | 0.20 | EN 14110 |
| Monoglyceride content | % (m/m) | — | 0.80 | EN 14105 |
| Diglyceride content | % (m/m) | — | 0.20 | EN 14105 |
| Triglyceride content | % (m/m) | — | 0.20 | EN 14105 |
| Free glycerol | % (m/m) | — | 0.02 | EN 14105 |
|  |  |  |  | EN 14106 |
| Total glycerol | % (m/m) | — | 0.25 | EN 14105 |
| Group I metals (Na + K) | mg/kg | — | 5.0 | EN 14108 |
|  |  |  |  | EN 14109 |
| Group II metals (Ca + Mg) | mg/kg | — | 5.0 | PrEN 14538 |
| Phosphorus content | mg/kg | — | 10.0 | EN 14107 |

Source: European Standard EN 14214: Automotive fuels - Fatty acid methyl esters (FAME) for diesel engines - Requirements and test methods (approved on 14 Feb. 2003)

Because they are usually the most economical raw material, fats and oils are commonly used as a feedstock for the esterification and/or transesterification reaction(s) to produce biodiesel. Fats and oils commonly undergo purification to remove contaminants prior to being used as the feedstock for biodiesel and other applications. The following patents relate to the purification of fats and oils.

U.S. Pat. No. 1,745,952 discloses a method to decolorize fats and oils. U.S. Pat. No. 2,401,339 discloses a method of removing impurities from fats, oils and waxes through the use of solid adsorbents and distillation. U.S. Pat. No. 3,862,054 discloses a method of removing phosphorus compounds and free fatty acids from vegetable oils. U.S. Pat. No. 5,252,762 discloses a method to remove contaminants (free fatty acids, soaps, phosphorus, metal ions and color bodies) from glyceride oils with a base treated adsorbent. All of the above described patents are directed to the purification of the fats and oils themselves, and not biodiesel or any other fatty acid alkyl esters. While fats and oils can be used as a feedstock for the production of biodiesel, the fats and oils do not constitute biodiesel.

As a result of the above-described transesterification reaction, two products are produced: fatty acid alkyl esters (FAAE) (typically Fatty Acid Methyl Esters) and glycerin. The glycerin portion is separated from the fatty acid alkyl esters (FAAE) portion, either by centrifugation or gravity settling, and the resulting fatty acid alkyl esters (FAAE) is referred to as crude biodiesel. The crude biodiesel portion consists of fatty acid alkyl esters (FAAE) containing impurities that must be removed before it can be commercially marketed as biodiesel. These impurities include, but are not limited to, alcohol, glycerin, soaps, residual catalyst, metals, free fatty acids, sterol glycosides as well as other impurities that reduce the stability of biodiesel. Therefore, at this point in the process, the fatty acid alkyl esters (FAAE) is not considered to be biodiesel and cannot be commercially marketed as biodiesel until the proper specifications (e.g. ASTM D6751, EN 14214, and the like) are achieved.

Conventional solutions to remove impurities from a crude biodiesel and produce a product that meets relevant specifications, include water wash, ion-exchange resin, and filtration using an adsorbent powder. Some conventional methods have combined the techniques to help achieve regulatory specifications. The unreacted methanol is removed from the crude biodiesel portion either prior to the purification process or after the purification process depending on which purification techniques) are used.

U.S. Patent Application Publication No. 2005/0018143 describes a process to produce a fatty acid alkyl ester for diesel fuel using water washing to remove the impurities. After the water washing process is completed, the fatty acid alkyl ester is treated with a high-water-absorptive resin to remove the water from the fatty acid alkyl ester.

U.S. Pat. No. 4,371,470 describes a method for producing a high quality fatty acid ester by esterification process, water washing to remove impurities and using an adsorbent to remove color from the fatty acid ester. The adsorbent is described as either activated clay or a mixture of activated clay and activated carbon.

The drawbacks of water wash are the large volume of fresh water needed to treat the biodiesel, the long amount of time required to treat the biodiesel, the potential for emulsion formation and resulting waste, and the large volume of wastewater either to be disposed of or treated.

Various patents describe purification of biodiesel, esters and related chemicals using adsorbents such as clay, carbon, silicon based adsorbents, such as magnesium silicate and zeolites.

U.S. Pat. No. 6,982,340 describes a process for purifying an ester with adsorption-treating with clay/activated carbon and a hydrogenating decomposition-type adsorbent using a carrier. The adsorbents in this process are used for the removal of sulfur compounds from an ester, not biodiesel. Even though biodiesel is a type of ester, there are numerous ester compounds not associated with biodiesel.

U.S. Patent Application Publication No. 2005/0081436 describes a method by which biodiesel is purified using an adsorptive filtration process using synthetic magnesium silicate.

U.S. Patent Application Publication No. 2005/0188607 describes a system for the removal of methanol from crude biodiesel using adsorptive filtration with a silicon based adsorbent (e.g. magnesium silicate). The removal of glycerin, and sodium or potassium hydroxide is also included.

U.S. Patent Application Publication No. 2006/0260184 describes an apparatus and process to refine biodiesel fuel through the use of an adsorbent material (e.g. magnesium silicate). This process also uses filtration.

U.S. Pat. No. 5,401,862 describes a process for the decolorization of fatty acid esters particularly the fatty acid esters suitable for use in foods and cosmetics. A solution of fatty acid ester dissolved in a polar solvent is passed through a column containing an adsorbent (mixture of montmorillonite clay and group consisting of silica gel and activated carbon). The solvent is then eliminated from the ester. The only contaminant claimed to be removed from this process is color.

U.S. Pat. No. 4,049,688 describes a method by which saturated esters of fatty acids can be separated from unsaturated esters through use of selective adsorption using an X or Y Zeolite.

The major drawback of adsorbent treatment of biodiesel is the disposal of the spent adsorbent filter cake.

None of these patents describe a continuous process using column purification or adsorbent regeneration. It is desirable to provide a continuous process for the purification of biodiesel. It is further desirable to provide a process that once charged with adsorbent comprises a closed system requiring no fresh water or new adsorbent for operation and generating no waste water or solid waste that needs to be treated or disposed of. Such a system is both economical and environmentally friendly.

A regenerable column adsorption system has been described. U.S. Pat. No. 6,635,595 describes a process for simultaneous alkyl esterification of edible oil and regeneration of spent oil purification medium. The process includes the simultaneous regeneration of spent clay and in situ recovery of oil from spent clay and conversion of the same to alkyl esters by treating the spent clay with alcohols. The process treats a mixture of spent clay (which contains residual oil from the edible oil refining processes) and vegetable oil such that the clay can be regenerated at the same time the oil is converted into alkyl esters. After this process, the regenerated spent bleaching earth is further activated at 120-500° C. for 2-6 hours so that it can be reused for the bleaching of vegetable oils (in refining process). The regeneration of the clay adsorbent material is described in this patent such that it could be reused in the vegetable oil refining process, but not in biodiesel purification.

SUMMARY OF THE INVENTION

A quick, economical and environmentally friendly, "green", process for the continuous purification of biodiesel (fatty acid alkyl esters (FAAE)) is described using a powdered, granulated or extruded adsorbent. The adsorbent is contained in a column system and is regenerated for reuse multiple times. The process employs an adsorbent such as, but not limited to, carbon, silica, clay, zeolite, or a metal silicate contained in one or more columns to remove the impurities from fatty acid alkyl esters (FAAE) or crude biodiesel in a continuous process. The process utilizes the adsorbent column system for the purification of biodiesel, rather than water or filtration, to remove soaps and other impurities entrained in crude biodiesel. The crude biodiesel is contacted with an adsorbent packed into a column, or multiple columns in series, for a sufficient amount of time to remove impurities such as, but not limited to, soaps, metals, free glycerin, sterol glycosides and many of the other impurities that reduce the stability of biodiesel. The resulting finished biodiesel exiting the column(s) is ready for the methanol recovery process. The life cycle of the adsorbent in the column(s) depends on the level of impurities in the incoming crude biodiesel, the quantity and adsorptive capacity of the adsorbent in the column(s), and the flow rate of the crude biodiesel through the column system. When the biodiesel exiting the column system no longer meets required specifications, the adsorbent is regenerated for reuse.

Regeneration of the adsorbent column is accomplished with a polar solvent such as methanol typically used in the transesterification process. The use of the same polar solvent for the regeneration step as the transesterification step provides for simplicity, economy, and cost containment through purchasing economies. The polar solvent is infused with a small quantity of acid, such as sulfuric acid, and passed through the adsorbent in the column to remove the adsorbed impurities contained in and on the adsorbent. The alcohol/acid is passed through the column and recycled back to the transesterification reaction until such time as little or no impurities are in the alcohol/acid filtrate. The adsorbent is then ready for reuse.

This regeneration process makes this system both economical and environmentally friendly. Regeneration and reuse of the adsorbent eliminates the large amounts of fresh water, resulting effluent, and/or solid filter cake waste produced during water or adsorbent filtration biodiesel purification processes. Biodiesel so treated results in a product acceptable to proceed to the methanol recovery step without the need for water washing or adsorptive treatment with filtration. The reclamation of the solvent used for regeneration further enhances the economics of the process and its environmental benefits.

Ion exchange resin, while very expensive, has been shown to effectively adsorb glycerin and remove some metals by ion exchange of metal for hydrogen, thereby converting metal soaps to free fatty acids. Because free fatty acids are released into the crude biodiesel filtrate after ion exchange treatment, careful monitoring of the treated crude biodiesel is required to insure that the acid value specification is met in the finished biodiesel if only ion exchange purification is used. It has further been shown that ion exchange resin may be regenerated for reuse for removal of glycerin from crude biodiesel but it cannot be regenerated for reuse for the removal of metals from crude biodiesel (see Table 2). When used alone in a biodiesel process, the ion exchange resin must be disposed of when the resin becomes saturated with metals. For this reason, ion exchange resin is not economically suitable by itself for the purification of crude biodiesel. However, it may be used as a pretreatment to remove glycerin from crude biodiesel prior to further processing by passing through the adsorbent column for removal of soaps, metals, and other impurities.

Ion-exchange resin may be packed into one or more columns and can be used first in series for treatment of the biodiesel before the biodiesel is contacted with the adsorbent column(s). Alcohol can also be used for the regeneration of the ion-exchange resin. The alcohol/impurities mixture from the ion-exchange resin column containing alcohol, glycerin and residual fatty acid alkyl esters (FAAE) can be directed to a settling tank to separate the glycerin from the alcohol and residual FAAE. The alcohol/acid/impurities mixture from the adsorbent column containing alkyl soaps, metals, glycerin and residual fatty acid alkyl esters (FAAE) can be directed to a reaction vessel and reacted with an acid, such as sulfuric acid, in the previously described esterification reaction prior to being directed to the settling tank to separate the glycerin and other impurities from the alcohol and residual FAAE. The acid selected for the esterification reaction may be the same as selected for the regeneration process in order to provide for simplicity, economy, and cost containment through purchasing economies of scale.

The invention will be more fully described by reference to the following drawings.

DETAILED DESCRIPTION

Figure 1:
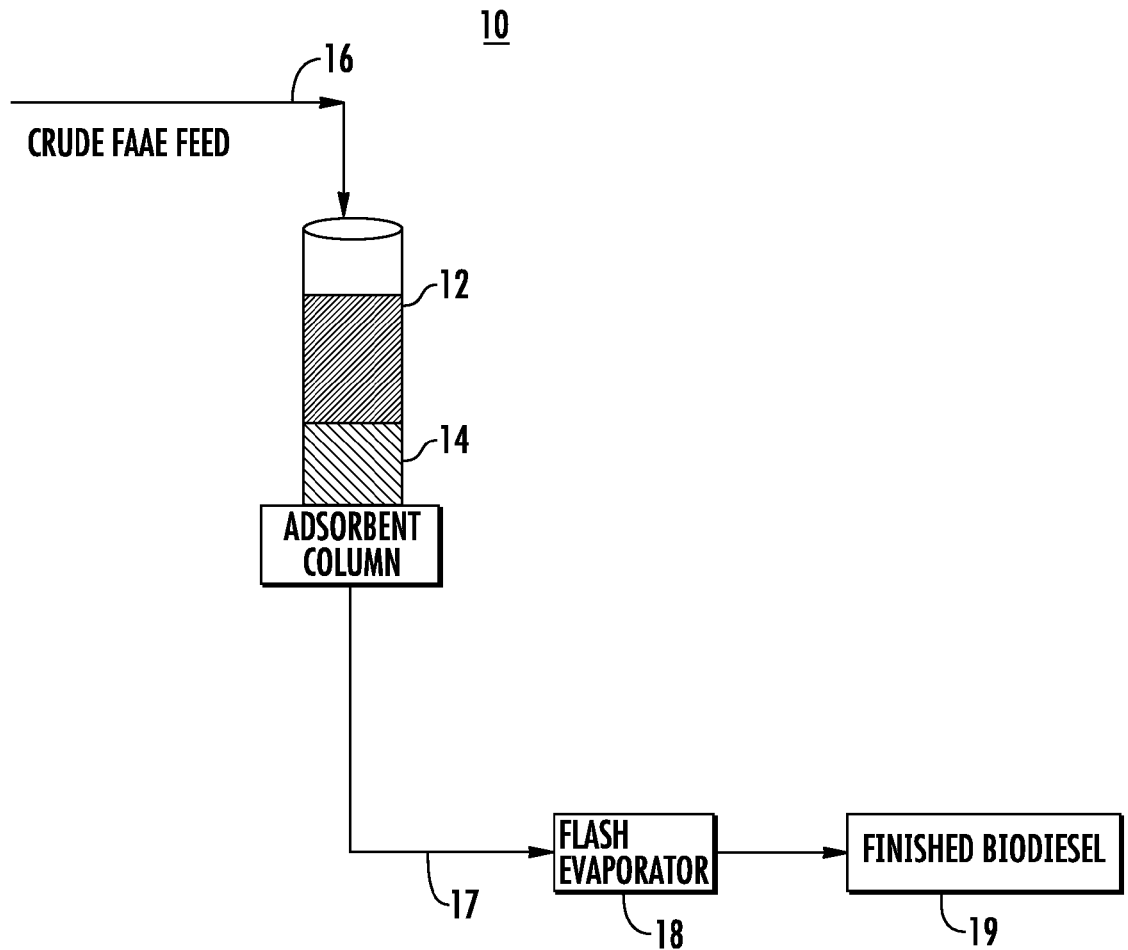
FIG. 1 is a schematic diagram of a system for biodiesel purification using an adsorbent column purification method in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a schematic diagram of continuous biodiesel purification by adsorbent system 10 in accordance with the teachings of the present invention. In a first embodiment, a single adsorbent column 12 packed with adsorbent material 14 is used to purify crude biodiesel 16. Crude biodiesel 16 comprises a crude feed of fatty acid alkyl esters (FAAE). Crude biodiesel 16 is contacted with a sufficient amount of adsorbent material 14 for a sufficient amount of time to remove impurities, such as, but not limited to soaps, catalyst, metals, free glycerin, sterol glycosides and other impurities that reduce the stability of biodiesel. Suitable adsorbent materials 14 include carbon, silica, metal silicate, zeolite, bleaching clay and activated bleaching clay. In a preferred embodiment, the adsorbent material is synthetic magnesium silicate.

Purified biodiesel 17 exiting adsorbent column 12 is a purified biodiesel suitable to proceed to methanol recovery without the need for water washing or adsorptive treatment with filtration. Purified biodiesel 17 exiting adsorbent column 12 is fed to flash evaporator 18. Flash evaporator 18 recovers alcohol, for example, methanol, from purified biodiesel 17 to produce finished biodiesel product 19.

During the column adsorption purification step, crude biodiesel 16 flows through column 12 until such time as adsorbent material 14 no longer removes sufficient impurities from crude biodiesel 16. This is determined by comparing the level of impurities in crude biodiesel 16 entering adsorbent column 12 to those in purified biodiesel 17 exiting adsorbent column 12. At such time as purified biodiesel 17 exiting adsorbent column 12 no longer meets the required specification or desired parameters, a regeneration of adsorbent material 14 is performed.

Figure 2:
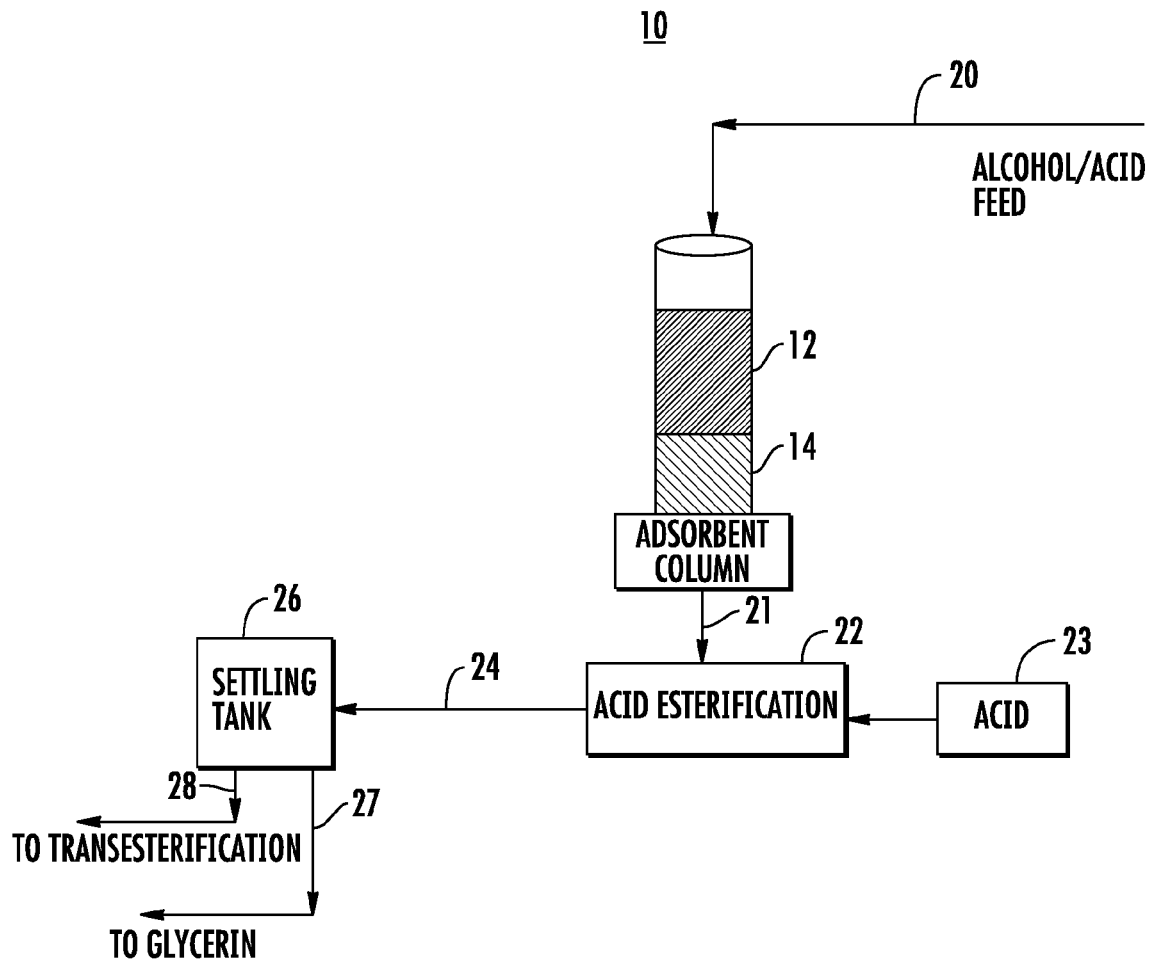
FIG. 2 is a schematic diagram of the system for biodiesel purification during regeneration of the adsorbent.

During regeneration, crude biodiesel 16 feed is stopped from adsorption column 12 and adsorbent material 14 within adsorbent column 12 is regenerated, as shown in FIG. 2. Solvent feed 20 is passed through adsorbent column 12 until such time that mixture 21 exiting adsorbent column 12 contains an acceptable impurity level, such as an impurity level having a value of zero, indicating that most if not all impurities have been stripped for the impurity saturated adsorbent. A suitable solvent feed 20 is a solution of a solvent containing an acid. In one embodiment, the solvent is alcohol. For example, the solvent can be methanol. In one embodiment, the acid is sulfuric acid, citric acid, or malic acid. The amount of acid added to the alcohol is about 0.005% to about 3.00% by weight.

After regeneration, mixture 21 exiting adsorbent column 12 is directed to acid esterification vessel 22 and is reacted with acid 23. Acid 23 selected for the esterification reaction in esterification vessel 22 can be the same or different than the acid described above used in regeneration of the adsorbent. For example, a suitable acid 23 is sulfuric acid. Acid 23 is used as a catalyst to directly esterify the corresponding alkyl soaps into crude fatty acid alkyl esters (FAAE). Mixture 24 exiting esterification vessel 22 comprises alcohol, fatty acid alkyl esters (FAAE), glycerin, excess acid, and water. Mixture 24 is sent to settling tank 26 to separate glycerin and other impurities from alcohol/fatty acid alkyl esters (FAAE). Mixture 24 is separated into glycerin/impurities phase 27 and alcohol/FAAE phase 28. Glycerin/impurities phase 27 is combined with the glycerin phase from the transesterification reaction. Alcohol/FAAE phase 28 can be sent directly to the transesterification reaction for further processing.

After the regeneration of adsorbent material 14, adsorbent column 12 is restarted by passing crude biodiesel 16 through adsorbent column 12 as shown in FIG. 1. While regeneration is performed on a first adsorbent column 12, the use of a second adsorbent column can be employed for the purification process while the first column is being regenerated providing for a continuous process.

Figure 3:
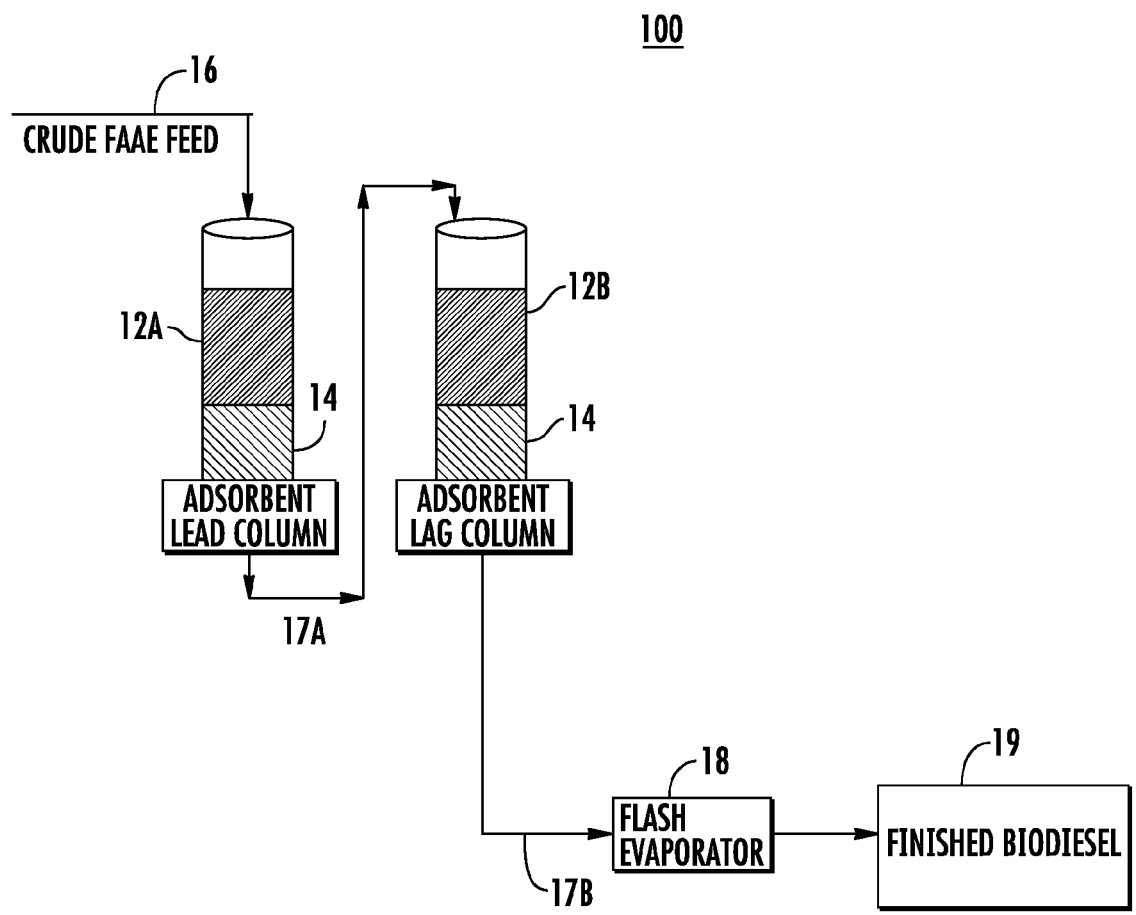
FIG. 3 is a schematic diagram of an alternative embodiment of a system for biodiesel purification using multiple adsorbent columns in accordance with the teachings of the present invention.

In a second embodiment, a plurality of adsorbent columns 12a-12b packed with adsorbent material 14 are used in series to purify crude biodiesel 16 in system 100, as shown in FIG. 3. The use of multiple adsorbent columns allows for a continuous process. After crude biodiesel 16 is separated from glycerin, it is contacted with adsorbent material 14 in lead adsorbent column 12a. Purified biodiesel 17a exiting adsorbent column 12a is contacted with adsorbent material 14 in lag adsorbent column 12b containing adsorbent material 14 to intercept impurities remaining in the crude biodiesel. Purified biodiesel 17*b* exiting adsorbent column 12*b* is subjected to flash evaporation to remove residual alcohol.

Figure 4:
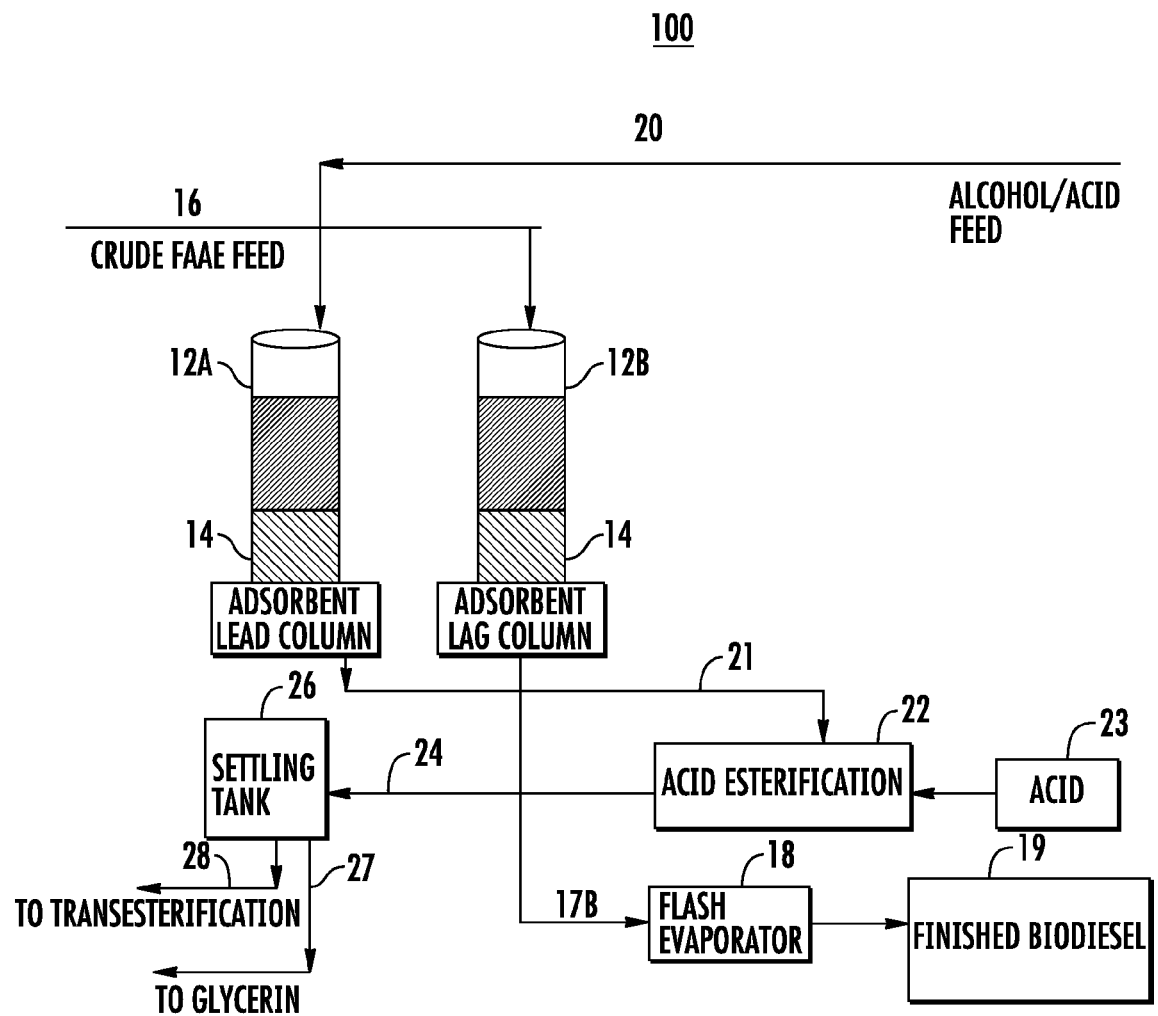
FIG. 4 is a schematic diagram of the system shown in FIG. 3 in which the lead column of FIG. 3 is being regenerated.

During the column adsorption purification step, crude biodiesel 16 flows through adsorbent column 12*a* until such time as adsorbent material 14 no longer removes sufficient impurities from crude biodiesel 16. This is determined by comparing the level of impurities in the crude biodiesel entering adsorbent column 12*a* to those in purified biodiesel 17*a* exiting adsorbent column 12*a*. At such time as purified biodiesel 17*a* exiting adsorbent column 12*a* no longer meets the required specification or desired parameters, regeneration of adsorbent material 14 is performed in lead adsorbent column 12*a*, as shown in FIG. 4. During regeneration, first lag column 12*b* in the series becomes the new lead column and any subsequent lag column(s) are moved up in the order of contact. Adsorbent material 14 in the original lead adsorbent column 12*a* is regenerated for reuse and becomes the last column in system 100.

Figure 5:
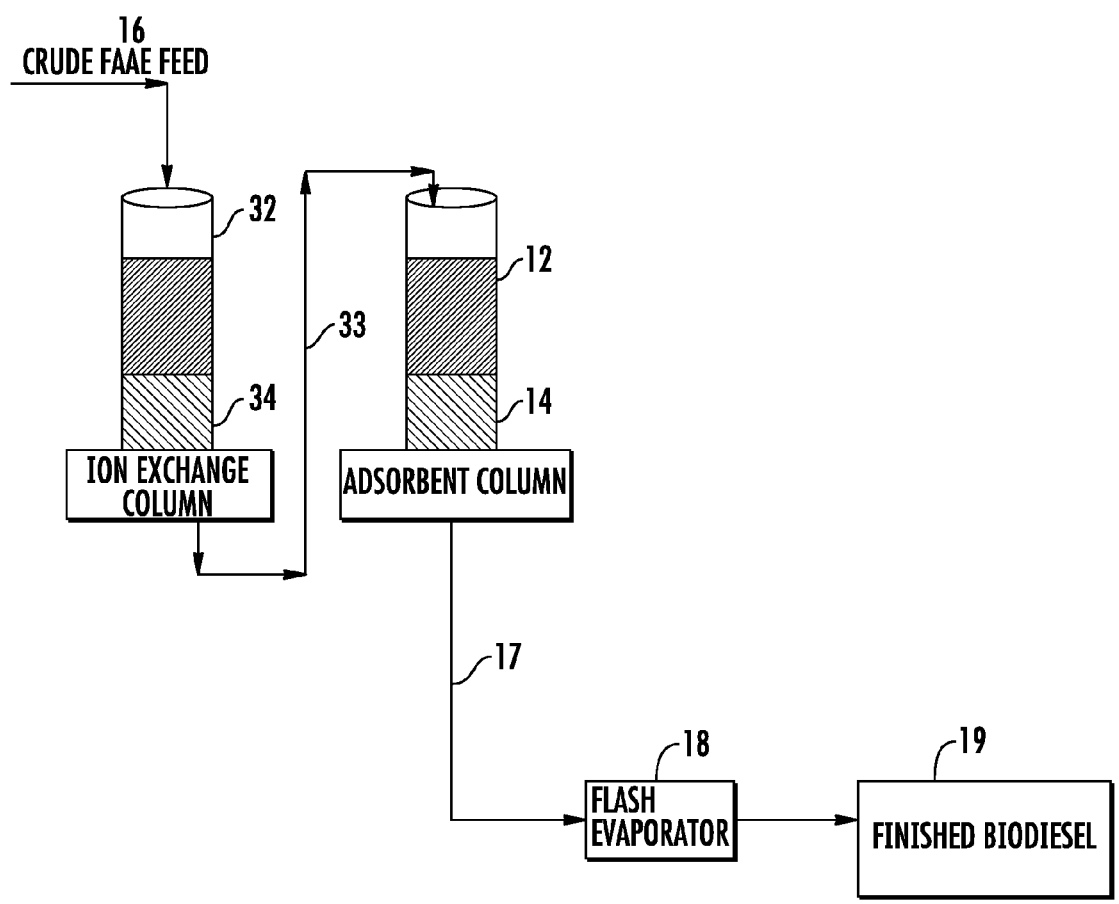
FIG. 5 is a schematic diagram of an alternative embodiment of a system for biodiesel purification using an ion-exchange and adsorption column purification method in accordance with the teachings of the present invention.

In a third embodiment, one or more adsorbent column(s) 12 containing adsorbent material 14 and one or more ion-exchange column(s) 32 containing an ion-exchange resin 34 are used in series to purify crude biodiesel 16 in system 200, as shown in FIG. 5. The ion-exchange resin can be cationic. One or more ion-exchange resin column(s) 32 are used first in the series to intercept any free glycerin and some of the metals from the alkyl soaps remaining in crude biodiesel 16. The resulting biodiesel 33 is then passed through one or more adsorbent column(s) 12 packed with adsorbent material 14 to remove the remaining impurities resulting in purified biodiesel 17 suitable to proceed to methanol recovery without the need for water washing or adsorptive treatment with filtration.

Figure 6:
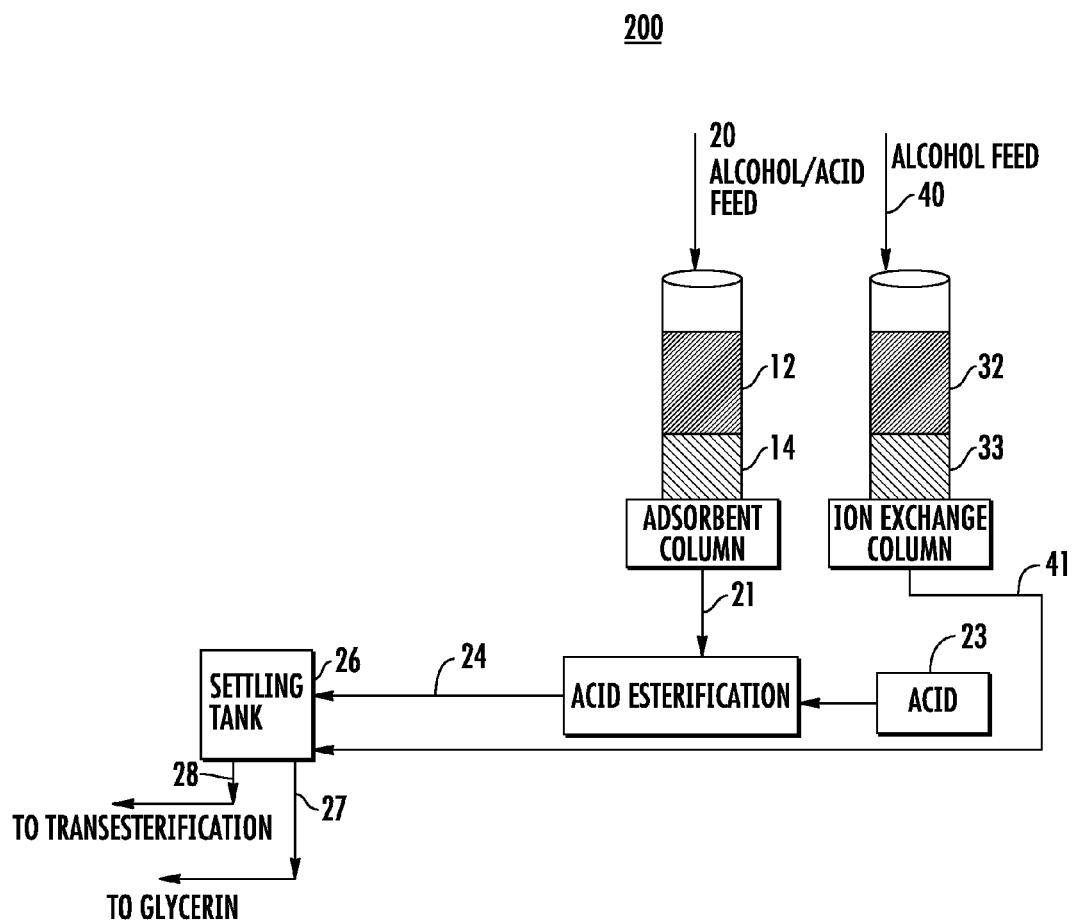
FIG. 6 is a schematic diagram of the system shown in FIG. 5 during regeneration of the ion-exchange and/or adsorbent columns.

The crude biodiesel is contacted in one or more ion-exchange column(s) 32 and adsorbent column(s) 12 and until such time as the ion-exchange resin and/or adsorbent material 14 no longer remove sufficient impurities from crude biodiesel 16. This is determined by comparing the level of impurities in crude biodiesel 16 entering ion-exchange column(s) 32 and/or adsorbent column(s) 12 to those in biodiesel 33 and purified biodiesel 17 exiting the respective columns. At such time as biodiesel 33 and purified biodiesel 17 exiting ion-exchange column(s) 32 and/or adsorbent column(s) 12 no longer meets the desired specifications or parameters, a second identical set of ion-exchange column(s) 32 and/or adsorbent exchange column(s) 12 is employed. While employing the second set of columns, the ion-exchange resin and/or adsorbent in the first set of columns are regenerated for re-use, as shown in FIG. 6. After the regeneration process, ion-exchange column(s) 32 and adsorbent column(s) 12 are ready for reuse and can be brought back on stream as a second set of columns, as desired.

Regeneration of ion-exchange resin column 32 is accomplished with a polar solvent such as alcohol, typically methanol, used in the transesterification process and is passed through ion-exchange column(s) 32 to remove primarily glycerin, contained in and on ion-exchange resin 33. The solvent is passed through ion-exchange column(s) 32 until such time as little or no glycerin is in the solvent filtrate 41.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

EXAMPLE 1

Single Column Purification Using Adsorbent Materials

Crude biodiesel was passed through a single column containing 2 g adsorbent material. The two adsorbents used in the example were: synthetic magnesium silicate (MAGNESOL® D-SOL D60 from The Dallas Group of America, Whitehouse, N.J.) and an acid activated clay. A summary of the results obtained from these two products is shown in Table 1. The crude biodiesel was passed through the column until such time that the soap content of the biodiesel exiting the column was greater than 50 ppm. The value of 50 ppm soap was chosen as the cutoff point as it corresponds to the 5 ppm specification of metals (sodium+potassium).

At such time that the biodiesel exiting the column contained more than 50 ppm soap, the column treatment was stopped and either the synthetic magnesium or the acid activated clay in the column was regenerated. A solution containing 0.10% sulfuric acid (93%) in methanol was passed through the column until such time that the methanol/sulfuric acid mixture exiting the column contained a soap value of zero.

After the regeneration of the product, the column was restarted by passing the crude biodiesel through the column.

TABLE 1

Results for Single Column Purification Using Adsorbent Materials

| SINGLE COLUMN | Column Throughput (mL) | | % Treatment Cumulative | MAGNESOL D-SOL D60 | | |
| --- | --- | --- | --- | --- | --- | --- |
| | | | | Column Throughput (mL) | | |
| Column Loading 2 g | per Cycle | Cumulative | % Treatment Cumulative | per Cycle | Cumulative | % Treatment Cumulative |
| Initial Cycle | 203 | 203 | 1.095% | 569 | 569 | 0.391% |
| After 1st Regeneration | 617 | 820 | 0.271% | 510 | 1079 | 0.206% |
| After 2$^{nd}$ Regeneration | 303 | 1123 | 0.198% | 487 | 1566 | 0.142% |
| After 3$^{rd}$ Regeneration | 739 | 1862 | 0.119% | 833 | 2399 | 0.093% |
| After 4th Regeneration | 542 | 2404 | 0.092% | 773 | 3172 | 0.070% |
| After 5th Regeneration | 77 | 2481 | 0.090% | 799 | 3971 | 0.056% |
| After 6th Regeneration | 395 | 2876 | 0.077% | 1215 | 5186 | 0.043% |
| After 7th Regeneration | 346 | 3222 | 0.069% | 661 | 5847 | 0.038% |
| After 8th Regeneration | 415 | 3637 | 0.061% | 1005 | 6852 | 0.032% |

TABLE 1-continued

Results for Single Column Purification Using Adsorbent Materials

| SINGLE COLUMN | Column Throughput (mL) | | | MAGNESOL D-SOL D60 | | |
|---|---|---|---|---|---|---|
| | | | | Column Throughput (mL) | | |
| Column Loading 2 g | per Cycle | Cumulative | % Treatment Cumulative | per Cycle | Cumulative | % Treatment Cumulative |
| After 9th Regeneration | 401 | 4038 | 0.055% | 950 | 7802 | 0.028% |
| After 10th Regeneration | 0 | 4038 | 0.055% | 971 | 8773 | 0.025% |
| After 11th Regeneration | 95 | 4133 | 0.054% | 1171 | 9944 | 0.022% |
| After 12th Regeneration | 115 | 4248 | 0.052% | 794 | 10738 | 0.021% |
| After 13th Regeneration | 182 | 4430 | 0.050% | 1185 | 11923 | 0.019% |
| After 14th Regeneration | 418 | 4848 | 0.046% | 1175 | 13098 | 0.017% |
| AVERAGE mL | 404 | | | 873 | | |
| TOTAL mL | 4038 | | | 13098 | | |
| TOTAL g | 3634 | | | 11788 | | |
| % Treatment | 0.055% | | | 0.017% | | |

EXAMPLE 2

Comparative Examples of Ion-Exchange Resin for Regeneration

Crude biodiesel was passed through a single column containing 2 g ion-exchange resin. The crude biodiesel was passed through the column until such time that the soap content of the biodiesel exiting the column was greater than 50 ppm. The value of 50 ppm soap was chosen as the cutoff point as it corresponds to the 5 ppm specification of metals (sodium+potassium). The results are shown in Table 2.

At such time that the biodiesel exiting the column contained more than 50 ppm soap, the column treatment was stopped and an attempt to regenerate the ion-exchange resin in the column was made. A solution containing 0.10% sulfuric acid (93%) in methanol was passed through the column and the resulting soap content of the methanol exiting the column was periodically checked. There was no measurable soap content in the methanol/sulfuric acid exiting the column.

After passing 200 mL of the methanol/sulfuric acid through the column containing the ion-exchange resin, flow of crude biodiesel through the column was restarted by passing the crude biodiesel through the column. The resulting biodiesel exiting the column was again monitored for soap content, but was never below 50 ppm. These results show that the ion-exchange resin cannot be regenerated for soap removal from the crude biodiesel. However, the ion-exchange resins did remove free glycerin from the crude biodiesel after regeneration. Therefore, the regeneration of ion exchange resin applies only to free glycerin and not soaps or metals.

TABLE 2

Results for Column Treatment of Crude Biodiesel Using (ion-exchange resin)

| Amount through column (ml) | Time (min) | Flow Rate (ml/min) | Soap (ppm) | % Free Glycerin | Water (ppm) |
|---|---|---|---|---|---|
| Initial Startup | | | | | |
| 100 | 646 | 0.15 | 45 | 0.002 | 225 |
| 198 | 1428 | 0.14 | 68 | | |
| 273 | 2193 | 0.12 | 64 | | |
| 333 | 2577 | 0.13 | 199 | 0.009 | 435 |
| After 1st Regeneration | | | | | |
| 100 | 751 | 0.13 | 117 | | |
| 187 | 1262 | 0.15 | 233 | 0.012 | 304 |

EXAMPLE 3

Dual Column Purification Using Synthetic Magnesium Silicate

Crude biodiesel was passed through a two column system in series containing 2 g adsorbent material in each column. The two adsorbents used in the example were: synthetic magnesium silicate (MAGNESOL D-SOL D60 from The Dallas Group of America, Whitehouse, N.J.) and an acid activated clay. A summary of the results obtained from these two products is shown in Table 3. The crude biodiesel was passed through the column until such time that the soap content of the biodiesel exiting the column was greater than 50 ppm. The value of 50 ppm soap was chosen as the cutoff point as it corresponds to the 5 ppm specification of metals (sodium+potassium).

At such time that the biodiesel exiting the column contained more than 50 ppm soap, the column treatment was stopped and either the synthetic magnesium silicate or acid activated clay in the lead column was regenerated. A solution containing 0.10% sulfuric acid (93%) in methanol was passed through the column until such time that the methanol/sulfuric acid mixture exiting the column contained a soap value of zero.

After the regeneration of the product, the lag column became the new lead column and the regenerated lead column was placed back in series as the new lag column. Thereafter, crude biodiesel was passed through the column system.

TABLE 3

Results for Dual Column Purification Using Synthetic Magnesium Silicate

| TWO COLUMNS Column Loading | Column Throughput (mL) | | % Treatment | MAGNESOL D-SOL D60 Column Throughput (mL) | | % Treatment |
|---|---|---|---|---|---|---|
| 4 g | per Cycle | Cumulative | Cumulative | per Cycle | Cumulative | Cumulative |
| Initial Cycle | 1297 | 1297 | 0.343% | 1826 | 1826 | 0.243% |
| After 1st Regen. | 1432 | 2729 | 0.163% | 1744 | 3570 | 0.124% |
| After 2nd Regen. | 1209 | 3938 | 0.113% | 1257 | 4827 | 0.092% |
| After 3rd Regen. | 1631 | 5569 | 0.080% | 2486 | 7313 | 0.061% |
| After 4th Regen. | 1031 | 6600 | 0.067% | 1743 | 9056 | 0.049% |
| After 5th Regen. | 1288 | 7888 | 0.056% | 2944 | 12000 | 0.037% |
| After 6th Regen. | 655 | 8543 | 0.052% | 1797 | 13797 | 0.032% |
| After 7th Regen. | 1203 | 9746 | 0.046% | 3053 | 16850 | 0.026% |
| AVERAGE mL | 1218 | | | 2106 | | |
| TOTAL mL | 9746 | | | 16850 | | |
| TOTAL g | 8771 | | | 15165 | | |
| % Treatment | 0.046% | | | 0.026% | | |

EXAMPLE 4

Dual Column Purification Using Ion-Exchange Resin—Synthetic Magnesium Silicate

Crude biodiesel was passed through a two column system in series containing 2 g of a commercially available ion-exchange resin and 2 g synthetic magnesium silicate (MAGNESOL DSOL D60 from The Dallas Group of America, Whitehouse, N.J.) in each column. The ion-exchange resin was set as the lead column and the magnesium silicate was placed in the system as the lag column. The crude biodiesel was passed through the column until such time that the soap content of the biodiesel exiting the column was greater than 50 ppm. The value of 50 ppm soap was chosen as the cutoff point as it corresponds to the 5 ppm specification of metals (sodium+potassium). The results from this series of tests are shown in Table 4 below.

At such time that the biodiesel exiting the column contained more than 50 ppm soap, the column treatment was stopped and both the ion-exchange resin in the lead column and the synthetic magnesium silicate in the lag column were regenerated. The ion-exchange resin was regenerated according to the procedure described in embodiment 3 using pure methanol and the magnesium silicate was regenerated according to the procedure under the section "Regeneration of Adsorbent". A solution containing 0.10% sulfuric acid (93%) in methanol was passed through the column containing the synthetic magnesium silicate until such time that the methanol/sulfuric acid mixture exiting the column contained a soap value of zero.

After the regeneration of the product, both columns were placed back into series in the same order, with the ion-exchange resin as the lead column and the magnesium silicate as the lag column. Once again, crude biodiesel was passed through the column system.

TABLE 4

Results for Dual Column Purification

| TWO COLUMNS Column Loading | Column Throughput (mL) | | % Treatment |
|---|---|---|---|
| 4 g | per Cycle | Cumulative | Cumulative |
| Initial | 4173 | 4173 | 0.107% |
| After 1st Regen. | 2642 | 6815 | 0.065% |
| After 2nd Regen. | 2088 | 8903 | 0.050% |
| After 3rd Regen. | 735 | 9638 | 0.046% |
| After 4th Regen. | 1003 | 10641 | 0.042% |
| After 5th Regen. | 780 | 11421 | 0.039% |
| After 6th Regen. | 600 | 12021 | 0.037% |
| After 7th Regen. | 670 | 12691 | 0.035% |
| AVERAGE mL | 1586 | | |
| TOTAL mL | 12691 | | |
| TOTAL g | 11422 | | |
| % Treatment | 0.035% | | |

EXAMPLE 5

Regeneration of Adsorbent Using Methanol/Acid

Crude biodiesel was passed through a column containing 40 g synthetic magnesium silicate (MAGENSOL D-SOL D60 from The Dallas Group of America, Inc., Whitehouse, N.J.) at a rate of 20 mL/minute until the synthetic magnesium silicate powder contained 0.45 g soap per gram of adsorbent. The soap content of the crude biodiesel was 2094 ppm. Samples were taken of the biodiesel exiting the column throughout the test and analyzed for soap content, as shown in Table 5. Once the synthetic magnesium silicate reached the 0.45 g soap per gram of adsorbent, the column was stopped and the adsorbent saturated with soap was taken out of the column.

TABLE 5

Loading of Soap onto MAGNESOL D-SOL D60 (synthetic magnesium silicate)

| Sample | Soap (ppm) | mL Biodiesel | g Biodiesel | g Soap | Soap Adsorbed (ppm) |
|---|---|---|---|---|---|
| Initial | 2094 | | | | |
| 100 ml | 34 | 100 | 90 | 0.1854 | 2060 |
| 200 ml | 0 | 100 | 90 | 0.18846 | 2094 |
| 300 ml | 22 | 100 | 90 | 0.18648 | 2072 |
| 400 ml | 51 | 100 | 90 | 0.18387 | 2043 |
| 900 ml | 173 | 500 | 450 | 0.86445 | 1921 |
| 1400 ml | 218 | 500 | 450 | 0.8442 | 1876 |
| 1900 ml | 246 | 500 | 450 | 0.8316 | 1848 |
| 2400 ml | 227 | 500 | 450 | 0.84015 | 1867 |
| 2900 ml | 245 | 500 | 450 | 0.83205 | 1849 |
| 3400 ml | 312 | 500 | 450 | 0.8019 | 1782 |
| 3900 ml | 409 | 500 | 450 | 0.75825 | 1685 |
| 4400 ml | 492 | 500 | 450 | 0.7209 | 1602 |
| 4900 ml | 581 | 500 | 450 | 0.68085 | 1513 |
| 5400 ml | 693 | 500 | 450 | 0.63045 | 1401 |
| 5900 ml | 740 | 500 | 450 | 0.6093 | 1354 |
| 6400 ml | 792 | 500 | 450 | 0.5859 | 1302 |
| 6900 ml | 803 | 500 | 450 | 0.58095 | 1291 |
| 7400 ml | 703 | 500 | 450 | 0.62595 | 1391 |
| 7900 ml | 702 | 500 | 450 | 0.6264 | 1392 |
| 8400 ml | 635 | 500 | 450 | 0.65655 | 1459 |
| 8900 ml | 729 | 500 | 450 | 0.61425 | 1365 |
| 9400 ml | 615 | 500 | 450 | 0.66555 | 1479 |
| 9900 ml | 618 | 500 | 450 | 0.6642 | 1476 |
| 10400 ml | 624 | 500 | 450 | 0.6615 | 1470 |
| 10900 ml | 651 | 500 | 450 | 0.64935 | 1443 |
| 11400 ml | 681 | 500 | 450 | 0.63585 | 1413 |
| 11900 ml | 695 | 500 | 450 | 0.62955 | 1399 |
| 12400 ml | 700 | 500 | 450 | 0.6273 | 1394 |
| 12900 ml | 713 | 500 | 450 | 0.62145 | 1381 |
| TOTALS | | 12900 | 9810 | 18.00306 | |
| Amount of Soap adsorbed (g) per gram of adsorbent | | | | 0.4500765 | |

The synthetic magnesium silicate loaded with soap was split into 5 gram portions, each placed into smaller columns to be regenerated. The regeneration of the adsorbent was carried out using different concentrations of 93% sulfuric acid, citric acid and malic acid powder in methanol. The solutions of acid/methanol were passed through the adsorbent in the column until such time that the soap content of the solution exiting the column was approximately zero.

Table 6 summarizes the conditions and results of the regenerations using 93% sulfuric acid with methanol. Table 7 shows results for regenerations using citric acid with methanol. Table 8 shows results for regenerations using citric acid with methanol. It is clear from these results that the adsorbent is effectively stripped of the impurities adsorbed from crude biodiesel and, is therefore suitable for reuse in the purification of crude biodiesel.

TABLE 6

Summary of Conditions and Results Of Regeneration of MAGNESOL D-SOL D60 (synthetic magnesium silicate) Using Methanol/Sulfuric Acid

| Volume (ml) | Hr. | Min | Flow Rate (mL/min.) | Soap (ppm) |
|---|---|---|---|---|
| 0.10% w/w Sulfuric Acid in Methanol | | | | |
| 52 | 2 | 32 | 0.34 | 7926 |
| 104 | 5 | 3 | 0.34 | 1547 |
| 154 | 7 | 35 | 0.34 | 781 |
| 200 | 9 | 43 | 0.34 | 193 |
| 230 | 11 | 13 | 0.34 | 83 |
| 260 | 12 | 47 | 0.34 | 0 |
| 0.20% w/w Sulfuric Acid in Methanol | | | | |
| 27 | 1 | 27 | 0.31 | 13309 |
| 75 | 4 | 1 | 0.31 | 1889 |
| 100 | 5 | 5 | 0.33 | 957 |
| 131 | 6 | 36 | 0.33 | 167 |
| 163 | 8 | 11 | 0.33 | 0 |
| 0.39% w/w Sulfuric Acid in Methanol | | | | |
| 26 | 1 | 16 | 0.34 | 13060 |
| 55 | 2 | 40 | 0.34 | 1605 |
| 88 | 4 | 16 | 0.34 | 0 |

TABLE 7

Summary of Conditions and Results of Regeneration of MAGNESOL D-SOL D60 (synthetic magnesium silicate) Using Methanol/Citric Acid

| Volume (ml) | Hr. | Min | Flow Rate (mL/min.) | Soap (ppm) |
|---|---|---|---|---|
| 0.11% w/w Citric Acid in Methanol | | | | |
| 52 | 2 | 29 | 0.35 | 8134 |
| 104 | 4 | 57 | 0.35 | 3980 |
| 154 | 7 | 24 | 0.35 | 3991 |
| 200 | 9 | 11 | 0.36 | 720 |
| 258 | 12 | 2 | 0.36 | 184 |
| 312 | 14 | 42 | 0.35 | 0 |
| 0.23% w/w Citric Acid in Methanol | | | | |
| 56 | 2 | 46 | 0.34 | 8173 |
| 116 | 5 | 26 | 0.36 | 3519 |
| 169 | 8 | 13 | 0.34 | 1892 |
| 195 | 9 | 23 | 0.35 | 0 |
| 0.45% w/w Citric Acid in Methanol | | | | |
| 50 | 2 | 27 | 0.34 | 9061 |
| 100 | 4 | 55 | 0.34 | 5211 |
| 140 | 6 | 55 | 0.34 | 2526 |
| 195 | 9 | 36 | 0.34 | 0 |

TABLE 8

Summary of Conditions and Results of Regeneration of MAGNESOL D-SOL D60 (synthetic magnesium silicate) Using Methanol/Malic Acid

| Volume (ml) | Hr. | Min | Flow Rate (mL/min.) | Soap (ppm) |
|---|---|---|---|---|
| 0.11% w/w Malic Acid with Methanol | | | | |
| 49 | 2 | 29 | 0.33 | 8322 |
| 100 | 5 | 6 | 0.33 | 4691 |
| 125 | 6 | 18 | 0.33 | 4867 |
| 171 | 9 | 21 | 0.30 | 2544 |
| 200 | 10 | 18 | 0.32 | 2003 |
| 253 | 13 | 6 | 0.32 | 88 |
| 280 | 14 | 32 | 0.32 | 0 |
| 0.23% Malic Acid with Methanol | | | | |
| 29 | 1 | 23 | 0.35 | 12120 |
| 74 | 3 | 40 | 0.34 | 8409 |
| 119 | 5 | 56 | 0.33 | 3750 |
| 161 | 8 | 1 | 0.33 | 406 |
| 191 | 9 | 32 | 0.33 | 0 |

TABLE 8-continued

Summary of Conditions and Results of Regeneration of MAGNESOL D-SOL D60 (synthetic magnesium silicate) Using Methanol/Malic Acid

| Volume (ml) | Hr. | Min | Flow Rate (mL/min.) | Soap (ppm) |
|---|---|---|---|---|
| 0.40% Malic Acid with Methanol | | | | |
| 27 | 1 | 23 | 0.33 | 16614 |
| 72 | 3 | 40 | 0.33 | 7269 |
| 116 | 5 | 56 | 0.33 | 30 |
| 157 | 8 | 1 | 0.33 | 0 |

It is to be understood that the above-described embodiments are illustrative of only a few of the many possible specific embodiments, which can represent applications of the principles of the invention Numerous and varied other arrangements can be readily devised in accordance with these principles by those skilled in the art without departing from the spirit and scope of the invention.

What is claimed is:

1. A process for purification of fatty acid alkyl esters (FAAE) comprising:
   (a) treating fatty acid alkyl esters (FAAE) utilizing one or more adsorbent columns containing an adsorbent material for removing one or more impurities from the fatty acid alkyl esters (FAAE) and said fatty acid alkyl esters (FAAE) continuously flow through said one or more columns;
   (b) regenerating the adsorbent material with an acidic alcohol for removing adsorbed impurities from the adsorbent material, and
   (c) re-using the regenerated adsorbent material in step (a); wherein said impurities are selected from one or more of soap, metals, free glycerin, sterol glycosides, and free fatty acids (FFA).

2. The process of claim 1 wherein the adsorbent material is a powder or is granulated.

3. The process of claim 1 wherein the adsorbent material is selected from carbon, silica, zeolite, metal silicate, bleaching clay, and activated bleaching clay.

4. The process of claim 1 wherein the adsorbent material is synthetic magnesium silicate.

5. The process of claim 1 wherein the fatty acid alkyl esters (FAAE) is crude biodiesel.

6. The process of claim 1 wherein the alcohol is methanol.

7. The process of claim 1 wherein the acid is sulfuric acid, citric acid, or malic acid.

8. The process of claim 1 wherein the amount of acid added to the alcohol is about 0.005% to about 3.00% by weight.

9. The process of claim 1 wherein after the step of regenerating the adsorbent material, further comprising the step of directly esterfying the FFA in the solvent filtrate using an acid as a catalyst.

10. The process of claim 9 wherein the acid is sulfuric acid.

11. The process of claim 9 wherein the fatty acid alkyl esters (FAAE) produced by the esterification step are reclaimed.

12. The process of claim 10 wherein the reclamation comprises separating glycerin and/or impurities from the alcohol and the biodiesel and recycling the alcohol and the biodiesel to be used directly in a transesterification reaction.

13. The process of claim 11 wherein the separated glycerin and/or impurities from the reclamation are added to glycerin and/or impurities from the transesterification reaction.

14. The process of claim 1 further comprising the step of:
   pre-treating the fatty acid alkyl esters (FAAE) in one or more columns containing an ion-exchange resin before entering a lead column of said one or more adsorbent columns.

15. The process of claim 14 wherein the ion-exchange resin is cationic.

16. The process of claim 14 further comprising the steps of regenerating said ion-exchange resin thereby providing reuse of the ion-exchange resin.

17. The process of claim 16 wherein the step of regenerating the ion-exchange resin is performed with a solvent.

18. The process of claim 17 wherein the solvent is an alcohol.

19. The process of claim 17 wherein the alcohol is methanol.

20. The process of claim 16 wherein after the step of regenerating the ion-exchange resin further comprises the step of separating glycerin from the alcohol and residual FAAE and recycling the alcohol and residual FAAE to be used directly in a transesterification reaction.

21. The process of claim 20 wherein the glycerin from the separation process is added to glycerin and/or impurities from the transesterification process.

* * * * *